(12) United States Patent
Jung et al.

(10) Patent No.: US 7,964,790 B2
(45) Date of Patent: Jun. 21, 2011

(54) DYE FOR PHOTOELECTRIC DEVICE AND PHOTOELECTRIC DEVICE COMPRISING THE DYE

(75) Inventors: Won Cheol Jung, Yongin-si (KR); Eun Sung Lee, Yongin-si (KR); Sang Cheol Park, Yongin-si (KR); Young Jun Park, Yongin-si (KR); Byung Hee Sohn, Yongin-si (KR); Jung Gyu Nam, Yongin-si (KR); Hye Suk Jo, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 1008 days.

(21) Appl. No.: 11/737,508

(22) Filed: Apr. 19, 2007

(65) Prior Publication Data
US 2008/0110496 A1    May 15, 2008

(30) Foreign Application Priority Data
Nov. 15, 2006  (KR) .................. 10-2006-0112778

(51) Int. Cl.
*H01L 51/46* (2006.01)
*C07C 223/01* (2006.01)

(52) U.S. Cl. .......... 136/263; 136/243; 136/252; 438/82; 438/57; 546/8

(58) Field of Classification Search .............. 136/263; 546/255, 257; 438/57, 63, 82
See application file for complete search history.

(56) References Cited

U.S. PATENT DOCUMENTS

| 6,437,130 | B1 * | 8/2002 | Paidi et al. ..................... 546/8 |
| 2005/0139257 | A1 * | 6/2005 | Islam et al. ..................... 136/263 |
| 2007/0059940 | A1 * | 3/2007 | Islam et al. ..................... 438/719 |
| 2007/0209695 | A1 * | 9/2007 | Wang et al. ..................... 136/252 |

FOREIGN PATENT DOCUMENTS

JP         2005-330469 A  *  4/2005

* cited by examiner

*Primary Examiner* — Jennifer K. Michener
*Assistant Examiner* — Jayne Mershon
(74) *Attorney, Agent, or Firm* — Cantor Colburn LLP

(57) ABSTRACT

Disclosed herein are a novel dye for a photoelectric device and a photoelectric device comprising the dye. More particularly, the dye for a photoelectric device incorporates different quaternary ammoniums into a carboxyl or phosphoric acid-substituted bipyridyl ligand of the dye, and a photoelectric device comprising the same. The dye for a photoelectric device as disclosed herein exhibits improved photosensitivity and light absorbing characteristics, thereby making it possible to fabricate a highly efficient photoelectric device when the dye is included in the device.

12 Claims, 1 Drawing Sheet

FIGURE
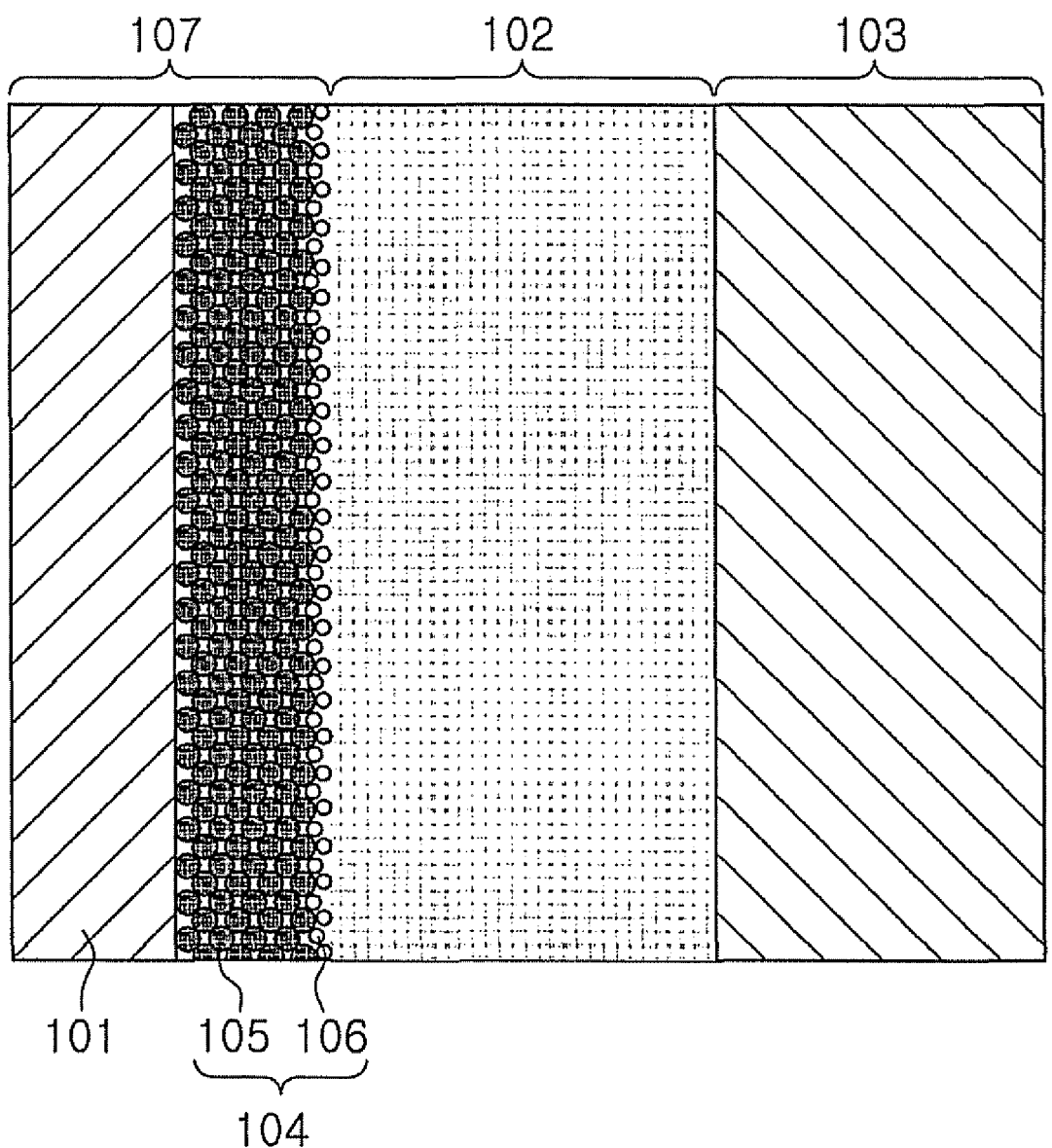

DYE FOR PHOTOELECTRIC DEVICE AND PHOTOELECTRIC DEVICE COMPRISING THE DYE

This non-provisional application claims priority to Korean Patent Application No. 10-2006-0112778, filed on Nov. 15, 2006, and all the benefits accruing therefrom under 35 U.S.C. §119(a) on, the content of which is herein incorporated by reference in its entirety.

BACKGROUND OF THE INVENTION

1. Field of the Invention

The present invention relates to a dye for a photoelectric device and a photoelectric device comprising the same. More particularly, the present invention relates to a novel dye for a photoelectric device showing improved energy conversion efficiency by incorporating different quaternary ammoniums into a bipyridyl ligand of the existing dye, and a photoelectric device comprising the same.

2. Description of the Related Art

In order to solve recent energy problems, extensive research on alternative energy resources that are capable of replacing existing fossil fuels is actively underway. In particular, to replace oil resources that are doomed to be exhausted within several decades, various attempts have been made to develop schemes for utilizing natural energy resources such as wind force, nuclear energy, solar energy, and the like.

Among these, a solar cell, which is a photoelectric device capable of converting solar energy into electric energy, is unlimited and environmentally favorable differently from any other resources, so it has been in the spotlight since the silicon solar cell was developed in 1983. Solar cells may be made of several types of raw materials, but of the possible materials, a solar cell based on silicon is most popular in the market. However, silicon solar cells have several problems in that it is hard to put to them to practicable use because production costs are very expensive, and improving energy conversion efficiency has proven difficult. Accordingly, in order to overcome these problems of the existing solar cells, the development of a dye-sensitized solar cell that can be fabricated at extremely low cost has been considered.

Unlike the silicon solar cell, the dye-sensitized solar cell is a photoelectrochemical solar cell that comprises, as its main ingredients, a photosensitive dye molecule capable of generating an electron-hole pair by absorbing visible light, and a transition metal oxide layer delivering the generated electrons. Since its production cost per unit of electric power is significantly low when compared with the existing silicon solar cell, the dye-sensitized solar cell has been receiving a great deal of attention as there is a possibility that it may prove useful as a substitute for existing solar cells.

Among the ingredients constituting the dye-sensitized solar cell, the dye molecule functions to generate excited-state electrons by absorbing visible light, and produces electromotive force by injecting the excited-state electrons into the conduction band of the transition metal oxide layer, and therefore the dye plays a very important role in the fabrication of a high-performance solar cell. Thus, there is an urgent need to develop a dye showing superior photosensitivity and improved light absorption efficiency, and therefore there is a great deal of interest in the development of such a new dye.

BRIEF SUMMARY OF THE INVENTION

Therefore, exemplary embodiments of the present invention have been made in view of the above problems of the prior art, and in one embodiment, a novel dye for a photoelectric device is provided that shows improved light absorption efficiency with high photosensitivity to sunlight.

In another embodiment, a photoelectric device comprising the dye is provided.

In accordance with one embodiment, there is provided a dye for a photoelectric device comprising two or more different quaternary ammoniums introduced into a bipyridyl ligand of the existing dye. Specifically, in an embodiment, a dye for a photoelectric device is represented by the following Formula 1:

  [Formula 1]

wherein L is 2,2'-bipyridyl-4,4'-dicarboxylic acid or 2,2'-bipyridyl-4,4'-diphosphonic acid; A is a quaternary ammonium; A' is a quaternary ammonium different from A; m is greater than or equal to 1; n is greater than or equal to 1; and the sum of m and n is greater than or equal to 2 and less than or equal to 4.

According to an embodiment, the quaternary ammoniums are characterized by being independently selected from the group consisting of halogen-substituted or unsubstituted tetraalkylammonium, benzyltrialkylammonium, phenyltrialkylammonium, where the number of carbon atoms of an alkyl group bonded to the N atom is 1 to 20, and alkyl groups bonded to the same N atom have the same or different lengths; and where the quaternary ammoniums are different from each other.

In accordance with another embodiment, there is provided a photoelectric device comprising the dye of Formula 1.

According to an embodiment, the photoelectric device may comprise a photoanode including the dye; a cathode; and an electrolyte layer formed between the photoanode and the cathode.

According to another embodiment, the photoanode may comprise a transparent electrode; a metal oxide layer formed on a surface of the transparent electrode; and the dye according to the present invention which is adsorbed to the surface of the metal oxide layer opposite the transparent electrode.

According to yet another embodiment, the photoanode may further comprise one or more dyes known in the art but excluding the dye according to the present invention.

In another embodiment, a method of improving the efficiency of a photoelectric device comprises modifying a dye for a photoelectric device to have Formula 1, and disposing the dye on a surface of a photoanode, wherein the photoelectric device comprises the photoanode, a cathode, and an electrolyte layer formed between the surface of the photoanode having the dye and the cathode has a photoelectric conversion efficiency greater than that of a photoelectric device prepared in the same way but with a dye that does not have the structure of Formula 1.

BRIEF DESCRIPTION OF THE DRAWINGS

The above and other features and advantages of the present invention will be more clearly understood from the following detailed description taken in conjunction with the accompanying drawings, in which:

The FIGURE is a cross-sectional view schematically illustrating an exemplary photoelectric device according to an embodiment.

DETAILED DESCRIPTION OF THE INVENTION

Hereinafter, exemplary embodiments of the present invention will be explained in more detail with reference to the accompanying drawings.

It will be understood that when an element is referred to as being "on" another element, it can be directly on the other element or intervening elements may be present therebetween. In contrast, when an element is referred to as being "disposed on" or "formed on" another element, the elements are understood to be in at least partial contact with each other, unless otherwise specified.

The terminology used herein is for the purpose of describing particular embodiments only and is not intended to be limiting of the invention. As used herein, the singular forms "a", "an" and "the" are intended to include the plural forms as well, unless the context clearly indicates otherwise. The use of the terms "first", "second", and the like do not imply any particular order but are included to identify individual elements. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements and the thicknesses of layers and regions are exaggerated for clarity.

The dye for a photoelectric device is embodied by introducing two or more different quaternary ammoniums into a bipyridyl ligand of an existing dye structure. Such a dye can, for example, have a structure represented by the following Formula 1 (based on ruthenium di-thiocyanate), but is not particularly limited thereto:

$$RuL_2(NCS)_2A_mA'_n \quad \text{[Formula 1]}$$

wherein L is 2,2'-bipyridyl-4,4'-dicarboxylic acid or 2,2'-bipyridyl-4,4'-diphosphonic acid; A is a quaternary ammonium; A' is a quaternary ammonium different from A; m is greater than or equal to 1; n is greater than or equal to 1; and the sum of m and n is greater than or equal to 2 and less than or equal to 4.

In other words, the dye provided herein is obtained by introducing two or more different quaternary ammoniums to a bipyridyl ligand having a carboxyl group or a phosphate group of the existing dye in exchange for the proton of the carboxyl group or phosphate group. Such a dye having at least two nonidentical tetraalkyl ammoniums thus shows improved efficiency when compared with, for example, $RuL'_2(NCS)_2(Bu_4N)_2$ dye (where L' is 2,2'-bipyridyl-4,4'-dicarboxylic acid and Bu is n-butyl), which includes two of the same kind of quaternary ammoniums (e.g., tetra-n-butylammonium), and which is commercially available as N719 dye.

Any known quaternary ammonium groups can be used as A and A' without limitation. In an embodiment, different kinds of the quaternary ammoniums can be used. Particular examples of the quaternary ammonium include halogen-substituted or unsubstituted tetraalkylammonium, benzyltrialkylammonium, phenyltrialkylammonium, and the like. Here, the number of carbon atoms of the alkyl group bonded to N atom is 1 to 20, and alkyl groups bonded to the same N atom can be of the same or of different lengths.

In another embodiment, the number of quaternary ammoniums introduced in substitution for the H of a carboxyl group or a phosphate group of the bipyridyl ligand is 3 or more, that is, the sum of m and n is greater than or equal to 3 and less than or equal to 4. In a specific embodiment, A is tetrabutylammonium; A' is selected from the group consisting of tetramethylammonium, n-hexadecyltrimethylammonium and benzyltrimethylammonium; m is 2; and n is 1. It is believed that materials having such a structure as provided by the nonidentical tetraalkyl ammonium groups imparts sufficient flexibility to the dye to allow the dye so modified with nonidentical alkylammonium groups to couple to the metal oxide layer of a photoanode, and to thereby freely receive electrons from the resulting coupling of the oxidizing-reducing agent.

In an exemplary embodiment, dye of the present invention can be represented by one of the following Formulas 2 to 4, but is not limited thereto:

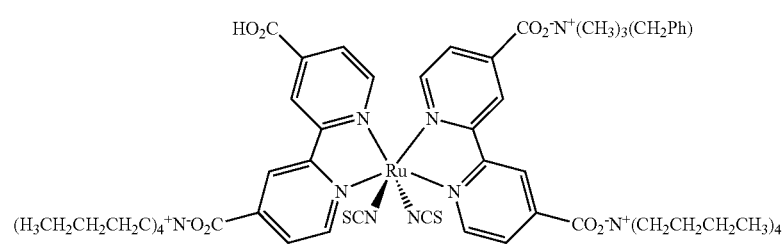

[Formula 2]

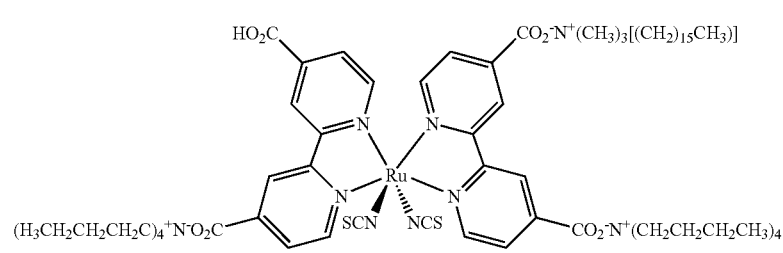

[Formula 3]

-continued

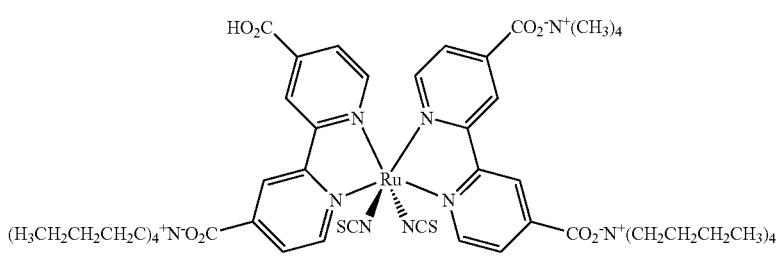

[Formula 4]

A dye according to exemplary embodiments disclosed herein can be prepared by a known synthesis method without limitation, and is preferably synthesized by the following procedure. In the synthetic procedure, the dye introduced with two or more different quaternary ammoniums according to exemplary embodiments can be obtained by diluting a compound containing one or more different kinds of quaternary ammonium groups except tetrabutylammonium group ("TBA"), for example, benzyltrimethylammonium hydroxide or n-hexadecyltrimethylammonium hydroxide, in a suitable solvent; mixing the diluent containing the quaternary ammonium groups with $RuL'_2(NCS)_2(Bu_4N)_2$ having two tetrabutylammonium (TBA) group substituents (where L' is 2,2'-bipyridyl-4,4'-dicarboxylic acid and Bu is n-butyl), which is commercially available as N719 dye, followed by reaction for an appropriate time; and removing the solvent and volatile materials from the reaction mixture.

The solvent employable in the above procedure can include, but is not particularly limited to, typical organic solvents such as acetonitrile, dimethylformamide ("DMF"), toluene, dichloromethane ($CH_2Cl_2$), triethylamine, dimethoxyether, tetrahydrofuran, and polar solvents such as alcohols including methanol, ethanol, tertiary-butanol and the like, and is used alone or in the form of a mixture. The dye used in the present invention is exemplified by $RuL'_2(NCS)_2(Bu_4N)_2$ dye (where L' is 2,2'-bipyridyl-4,4'-dicarboxylic acid and Bu is n-butyl), but there is no limitation on the kind of the dye so long as it can be used in the field of photoelectric devices, including $RuL''(NCS)_3(Bu_4N)_3$ dye (where L'' is 2,2':6',2''-terpyridine-4,4',4''-tricarboxylic acid and Bu is n-butyl), or a ruthenium compound such as an asymmetric ruthenium dye. Further, the reaction conditions may be determined appropriately by considering the kind of starting material and the use thereof; for instance, the reaction may be conducted at room temperature for 30 minutes to 24 hours.

In another embodiment, a photoelectric device comprising the dye according to the exemplary embodiment of the present invention is provided.

A photoelectric device comprising the dye showing improved photosensitivity and light absorption efficiency can exhibit superior performance when compared with an existing dye for a photoelectric device in terms of photoelectric conversion efficiency.

In particular, the photoelectric device of the present invention can comprise a photoanode including the dye for a photoelectric device according to the present invention; a cathode; and an electrolyte layer formed between the photoanode and the cathode.

The FIGURE is a cross-sectional view schematically illustrating the structure of the photoelectric device according to an embodiment. In particular, referring to the FIGURE, the photoelectric device can include a photoanode 107 including a transparent electrode 101, a metal oxide layer 105 formed on a surface of transparent electrode 101, and dye 106 according to the present invention, which is adsorbed to a surface of the metal oxide layer 105 opposite the transparent electrode 101; a cathode 103; and an electrolyte layer 102 disposed between the photoanode 107 and the cathode 103. At this time, the part composed of the metal oxide layer 105 and the dye 106 is generally referred to as a light absorbing layer 104.

As the transparent electrode, a transparent substrate may be used by itself or can have a conductive material coating its surface. However, in an embodiment, it is desirable to employ a transparent substrate coated with a conductive material thereon for reasons of conductivity. There is no limitation on the substrate so long as it is transparent, and nonrestrictive examples thereof can include a glass substrate, a plastic substrate, or the like. The conductive material coated on the transparent substrate can include indium tin oxide ("ITO"), fluorine-doped tin oxide ("FTO"), $ZnO$—$Ga_2O_3$, $ZnO$—$Al_2O_3$, $SnO_2$—$Sb_2O_3$, and the like, but the conductive material is not necessarily limited thereto.

The metal oxide layer disclosed herein can be selected from the group consisting of porous titanium oxides, niobium oxides, hafnium oxides, indium oxides, tin oxides, and zinc oxides, and used alone or in the form of a mixture thereof. Preferably, titanium oxide ($TiO_2$) can be used. Since it is desirable to enlarge the surface area of the metal oxide layer so that the dye adsorbed to the upper portion of the metal oxide layer can absorb more light, it is also desirable that the metal oxide layer includes a nano-structure such as a nanotube, a nanowire, a nanobelt, or a nanoparticle.

Further, the surface of the metal oxide layer can be in the form of a planar structure or an uneven structure, and, in particular, in case where the surface has an uneven structure, its surface area is significantly increased, thereby allowing sufficient adsorption to or contact with the dye or the electrolyte. Examples of the uneven structure may include a stair shape, a needle shape, a mesh shape, a scar shape, or the like, but are not limited thereto.

The metal oxide layer can be prepared in the form of a monolayer or a multilayer using two kinds of metal oxides having a different particle size. For example, a double-layered metal oxide layer can be formed by coating with a metal oxide having a particle size of 9 to 20 nm in a thickness of 10 to 20 μm, and then coating with another metal oxide having a particle size of 200 to 400 nm in a thickness of 3 to 5 μm thereon.

The coating method of the metal oxide can be performed by a conventional coating method such as screen printing, spin coating, dipping, doctor blading, or the like, and after the coating is completed, the initial coating of the metal oxide can be followed by known drying and curing procedures. For example, the metal oxide may be dried at about 50 to 100° C. in the drying procedure and cured at about 400 to 500° C. in the curing procedure.

Meanwhile, the photoanode can further comprise one or more known dyes that are not identical to the dye according to the embodiment. That is, the photoanode included in the photoeletronic device according to the present invention can further comprise one or more dyes useful in the field of solar cells, particularly ruthenium complexes; xanthine-based dyes including rhodamine B, Rose bengal, eosin, or erythrosine; cyanine-based dyes including quinocyanine or cryptocyanine; basic dyes including phenosafranine, capri blue, thiosine, or methylene blue; porphyrin-based compounds including chlorophyll, zinc porphyrin, or magnesium porphyrin; azo dyes; phthalocyanine compounds; Ru trisbipyridyl complexes; anthraquinone-based dyes; or polycyclic quinine-based dyes.

The photoanode may be prepared by a method known in the field of photoelectronic devices, for instance, by coating the surface of a transparent substrate, previously coated with a conductive material, with porous metal oxide and then curing to thereby form a metal oxide layer; and soaking the metal oxide layer in a solution of the dye according to the present invention, for a time appropriate to induce adsorption of the dye onto the surface of the metal oxide layer.

There is no limitation to the material for the cathode so long as it is a conductive material. An insulating material can be used if a conductive layer is formed on the side opposite to the photoanode. In an embodiment, an electrochemically stable material is useful as a cathode, including in an exemplary embodiment platinum, gold, carbon, or the like.

To improve catalytic effect of oxidation-reduction, the cathode surface on the opposite side of the photoanode can, in an embodiment, have a microstructure so as to provide an enlarged surface area. For example, platinum that is in platinum black state or carbon that is in porous state is preferred. The platinum black can be formed by an anodizing method of platinum or treatment of platinum with chloroplatinic acid, and porous carbon can be prepared by sintering carbon nanoparticles or curing organic polymers.

There is no limitation on the kind of an electrolyte solution constituting the electrolyte layer so long as it exhibits hole conductivity, and particular examples thereof may include acetonitrile solution of iodide, NMP solution, 3-methoxypropionitrile, and the like, but are not necessarily limited thereto.

The photoelectric device of the present invention and having such a structure may be fabricated by a known general method without limitation. In particular, the photoelectric device of the present invention may be fabricated by the steps of: preparing a photoanode; providing a cathode proximate to and coplanar with the photoanode; and forming an electrolyte layer between and in at least partial contact with a surface of each of the photoanode and the cathode.

In another embodiment, a method of improving the efficiency of a photoelectric device comprises modifying a dye for a photoelectric device to have Formula 1, and disposing the dye on a surface of a photoanode, wherein the photoelectric device comprises the photoanode, a cathode, and an electrolyte layer formed between the surface of the photoanode having the dye and the cathode has a photoelectric conversion efficiency greater than that of a photoelectric device prepared in the same way but with a dye that does not have the structure of Formula 1. The photoelectric conversion efficiency of a photoelectric device having the dye of Formula 1 can be greater than 7.5%.

Exemplary embodiments of the present invention will now be described in more detail with reference to the following examples. However, the examples are given for the purpose of illustration and are not to be construed as limiting the scope of the invention.

[Preparation of Dye]

PREPARATION EXAMPLE 1

12.55 mg of benzyltrimethylammonium hydroxide solution (TCI CO., Ltd., 40% by weight in methanol, 0.03 mmol) was poured into a 250-ml round shaped flask having a magnetic bar put therein at room temperature and diluted with 20 mL of methanol. Next, 35.64 mg (0.03 mmol) of $RuL'_2(NCS)_2(Bu_4N)_2$ dye (where L' is 2,2'-bipyridyl-4,4'-dicarboxylic acid and Bu is n-butyl) (N719 dye, Solaronix) was added to the flask, and the mixture was stirred and allowed to react for 2 hours. Then, the solvent was removed from the dye solution of $N3(TBA)_2(BzTMA)_1$ (where N3 represents cis-bis-isothiocyanato-bis(4,4-dicarboxylic acid-2,2-bipyridine)Ruthenium(II), TBA is tetrabutylammonium and BzTMA is benzyltrimethylammonium) represented by Formula 2 obtained above with a rotary evaporator. Subsequently, $N3(TBA)_2(BzTMA)_1$ was dissolved in 100 mL of a mixed solvent (10% acetonitrile and 90% tertiary-butanol, by volume) and stirred by using the magnetic bar at 650 rpm for 10 hours, to thereby obtain a dye solution.

$^1$H NMR ($CD_3OD$) δ(ppm) 1.01 (t, 24H), 1.45-1.55 (m, 16H), 1.62-1.75 (m, 16H), 3.11 (s, 9H), 3.20-3.30 (m, 16H), 4.53 (s, 2H), 7.50-7.58 (m, 5H), 7.59 (d, 2H), 7.71 (d, 2H), 8.23 (dd, 2H), 8.88 (s, 2H), 9.02 (s, 2H), 9.49 (d, 2H).

PREPARATION EXAMPLE 2

36.18 mg of hexadecyltrimethylammonium hydroxide (TCI Co., Ltd., 25% by weight in methanol, 0.03 mmol) was poured into a 250-ml round shape flask having a magnetic bar put therein at room temperature and diluted with 20 mL of methanol. Next, 35.64 mg (0.03 mmol) of $RuL'_2(NCS)_2(Bu_4N)_2$ dye (where L' is 2,2'-bipyridyl-4,4'-dicarboxylic acid and Bu is n-butyl) (N719 dye, Solaronix) was added to the flask, and the mixture was stirred and allowed to react for 2 hours. Then, the solvent was removed from the dye solution of $N3(TBA)_2(HDTMA)_1$ (where N3 represents cis-bis-isothiocyanato-bis(4,4-dicarboxylic acid-2,2-bipyridine)Ruthenium(H), TBA is tetrabutylammonium and HDTMA is hexadecyltrimethylammonium) represented by Formula 3 obtained above with a rotary evaporator. Subsequently, $N3(TBA)_2(HDTMA)_1$ was dissolved in 100 mL of a mixed solvent (10% acetonitrile and 90% tertiary-butanol by volume) and stirred by using the magntic bar at 650 rpm for 10 hours, to thereby obtain a dye solution.

$^1$H NMR ($CD_3OD$) δ(ppm) 1.05 (m, 27H), 1.28-1.50 (m, 42H), 1.61-1.82 (m, 18H), 3.12 (s, 9H), 3.22-3.30 (m, 16H), 7.63 (d, 2H), 7.72 (d, 2H), 8.25 (dd, 2H), 8.86 (s, 2H), 9.02 (s, 2H), 9.55 (d, 2H).

PREPARATION EXAMPLE 3

5.5 mg of tetramethylammonium hydroxide pentahydrate (Sigma-Aldrich Co., 0.03 mmol) was poured into a 250-ml round shape flask having a magnetic bar put therein at room temperature and dissolved in 20 mL of methanol. Next, 35.64 mg (0.03 mmol) of $RuL'_2(NCS)_2(Bu_4N)_2$ dye (where L' is 2,2'-bipyridyl-4,4'-dicarboxylic acid and Bu is n-butyl)(N719 dye, Solaronix) was added to the flask, and the mixture was stirred and reacted for 2 hours. Then, the solvent was removed from the dye solution of $N3(TBA)_2(TMA)_1$ (where N3 represents cis-bis-isothiocyanato-pentahydrate-bis(4,4-dicarboxylic acid-2,2-bipyridine)Ruthenium(II), TBA is tetrabutylammonium and TMA is tetramethylammonium) represented by Formula 4 obtained above with a rotary evaporator. Subsequently, N3(TBA)$_2$(TMA)$_1$ was dissolved in 100 mL of a mixed solvent (10% acetonitrile and 90% tertiary-butanol by volume) and stirred by using the magnetic bar at 650 rpm for 10 hours, to thereby obtain a dye solution.

$^1$H NMR (CD$_3$OD) δ(ppm) 1.05 (t, 24H), 1.30-1.48 (m, 16H), 1.60-1.75 (m, 16H), 3.15-3.30 (m, 28H), 7.63 (d, 2H), 7.71 (d, 2H), 8.25 (dd, 2H), 8.82 (s, 2H), 9.05 (s, 2H), 9.53 (d, 2H).

[Fabrication of a Photoelectric Device]

EXAMPLE 1

After fluorine-doped tin oxide (FTO) was coated on a glass substrate by using a sputter, a paste of TiO$_2$ particles having a particle size of 13 nm was coated once or several times thereon by using a screen printing method and cured at 450° C. for 30 minutes, to thereby form a porous TiO$_2$ membrane having 15 μm in thickness. In succession, the dye obtained in Preparation Example 1 was dissolved in the mixed solvent of butanol and acetonitrile (1:1 v/v) at a concentration of 0.3 mM, and then, the glass substrate having the TiO$_2$ membrane formed thereon was soaked in the mixture for 24 hours and dried so as to adsorb the dye to the whole surface of the TiO$_2$ membrane, to thereby prepare a photoanode.

Thereafter, a platinum membrane was deposited on the glass substrate coated with indium tin oxide (ITO) with a sputter, and microholes were made thereon for the injection of an electrolyte solution by using a drill having a diameter of 0.75 mm, to thereby prepare a cathode.

Next, the photoanode and the cathode thus prepared were assembled together. At this time, a polymer sheet having a thickness of 40 microns and composed of SURLYN® (Du-Pont Ltd.) was disposed between the photoanode and the cathode, and then, the two electrodes were compressed under pressure of about 1 to 3 bars on a heating plate at about 100 to 140° C. The polymer was tightly adhered to the surfaces of the two electrodes by heat and pressure.

Subsequently, an electrolyte solution was filled in the space between the two electrodes through the microholes formed thereon, to thereby prepare a photoelectric device. An electrolyte solution of I$^{3-}$/I$^-$, prepared to have component concentrations of 0.6 M in 1,2-dimethyl-3-propyloctyl-imidazoleium iodide, 0.2 M in LiI, 0.04 M in I$_2$ and 0.2 M in 4-tert-butyl pyridine (TBP) by dissolving appropriate amounts of each of these compounds in a common solution of acetonitrile to achieve these concentrations, was employed for this purpose.

EXAMPLE 2

The photoelectric device was fabricated by the same method as described in Example 1 except that the dye obtained in Preparation Example 2 was employed.

EXAMPLE 3

The photoelectric device was fabricated by the same method as described in Example 1 except that the dye obtained in Preparation Example 3 was employed.

COMPARATIVE EXAMPLE 1

The photoelectric device was fabricated by the same method as described in Example 1 except that RuL'$_2$(NCS)$_2$(Bu$_4$N)$_2$(where L' is 2,2'-bipyridyl-4,4'-dicarboxylic acid and Bu is n-butyl)(Solaronix) was used as a dye.

[Characteristic Assessment of a Photoelectric Device]

To assess photoelectric efficiency of each device prepared in Examples 1 to 3 and Comparative Example 1, photovoltage and photocurrent were first measured. A xenon lamp (Oriel, 01193) was utilized as a light source, and the irradiation condition (AM 1.5) of the xenon lamp was compensated with a standard solar cell (Furnhofer Institute Solare Engeriessysteme, Certificate No. C-ISE369, Type of material: Mono-Si+KG filter). Then, current density (I$_{sc}$), voltage (V$_{oc}$) and fill factor (FF) were calculated from the measured photocurrent-voltage curve, and photoelectric conversion efficiency (η$_e$) was calculated by the following Mathematical Formula 1. The results are given in Table 1 below.

$$\eta_e = (V_{oc} \cdot I_{sc} \cdot FF)/(P_{inc}) \quad \text{[Mathematical Formula 1]}$$

wherein P$_{inc}$ denotes 100 mw/cm$^2$ (1 sun).

TABLE 1

| | I$_{sc}$(mA/cm$^2$) | V$_{oc}$(mV) | FF(%) | Photoelectric conversion efficiency (%) |
|---|---|---|---|---|
| Example 1 | 12.565 | 780.0 | 0.782 | 7.800 |
| Example 2 | 11.826 | 789 | 0.784 | 7.567 |
| Example 3 | 13.32 | 775.29 | 0.799 | 8.531 |
| Comparative Example 1 | 11.531 | 776 | 0.760 | 7.073 |

As apparent from the foregoing, the dye for a photoelectric device according to exemplary embodiments of the present invention exhibits improved photosensitivity and light absorbing characteristics, as summarized in table 1 by improved photoelectric conversion efficiency, thereby making it possible to fabricate a highly efficient photoelectric device when applied to such a device, and where the device so prepared has improved efficiency over devices prepared without the improved dyes disclosed herein.

Although the preferred embodiments of the present invention have been disclosed for illustrative purpose, those skilled in the art will appreciate that various modifications, additions and substitutions are possible, without departing from the scope and spirit of the invention as disclosed in the accompanying claims.

What is claimed is:

1. A dye for a photoelectric device represented by the following Formula 1:

[Formula 1]

wherein L is 2,2'-bipyridyl-4,4'-dicarboxylic acid; A is a quaternary ammonium; A' is a quaternary ammonium different from A; m is greater than or equal to 1; n is greater than or equal to 1; and the sum of m and n is greater than or equal to 2 and less than or equal to 4, wherein the dye is represented by one of the following Formulas 2 to 4:

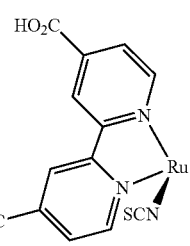
[Formula 2]

-continued

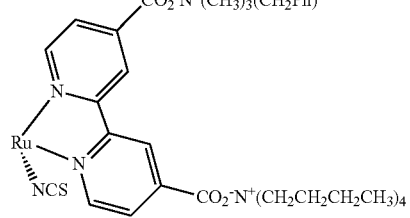

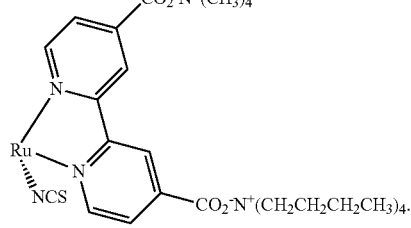

[Formula 3]

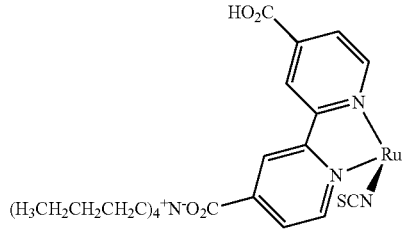

2. The dye for a photoelectric device according to claim 1, wherein A and A' are independently selected from the group consisting of halogen-substituted or unsubstituted tetraalkylammonium, benzyltrialkylammonium, and phenyltrialkylammonium, wherein the number of carbon atoms of an alkyl group bonded to the N atom is 1 to 20 and alkyl groups bonded to the same N atom have the same or different lengths.

3. The dye for a photoelectric device according to claim 1, wherein the sum of m and n is greater than or equal to 3 and less than or equal to 4.

4. The dye for a photoelectric device according to claim 1, wherein A is tetrabutylammonium; A' is selected from the group consisting of tetramethylammonium, n-hexadecyltrimethylammonium, and benzyltrimethylammonium; m is 2; and n is 1.

5. A photoelectric device comprising a photoanode including a dye for a photoelectric device represented by the following Formula 1; a cathode; and an electrolyte layer formed between the photoanode and the cathode:

$$RuL_2(NCS)_2A_mA'_n \qquad \text{[Formula 1]}$$

wherein L is 2,2'-bipyridyl-4,4'-dicarboxylic acid or 2,2'-bipyridyl-4,4'-diphosphonic acid; A is a quaternary ammonium; A' is a quaternary ammonium different from A; m is greater than or equal to 1; n is greater than or equal to 1; and the sum of m and n is greater than or equal to 2 and less than or equal to 4 wherein the dye is represented by one of the following Formulas 2 to 4:

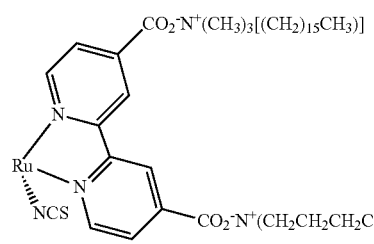

[Formula 4]

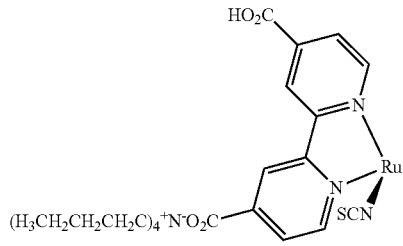

[Formula 2]

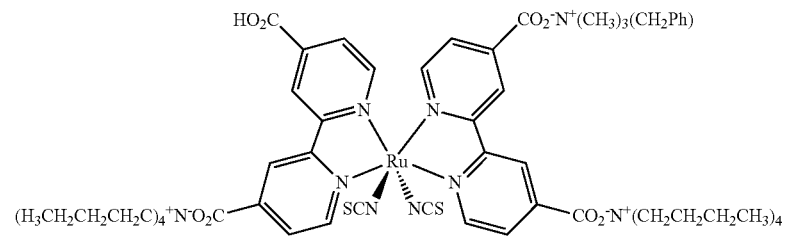

[Formula 3]

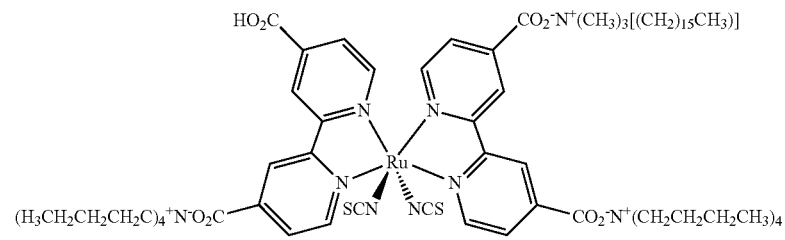

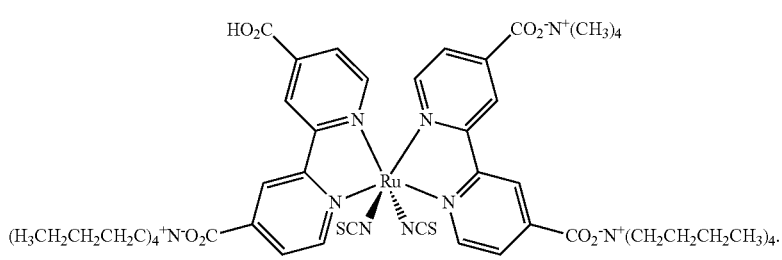

[Formula 4]

6. The photoelectric device according to claim 5, wherein the photoanode comprises a transparent electrode; a metal oxide layer formed on a surface of the transparent electorde; and the dye for a photoelectric device represented by Formula 1 as defined in claim 6 adsorbed to a surface of the metal oxide layer opposite the transparent electrode.

7. The photoelectric device according to claim 6, wherein the transparent electrode is a transparent substrate coated with a conductive material thereon.

8. The photoelectric device according to claim 5, wherein the photoanode further comprises one or more dyes selected from the group consisting of ruthenium complexes; xanthine-based dyes; cyanine-based dyes; basic dyes; porphyrin-based compounds; azo dyes; phthalocyanine compounds; Ru tris-bipyridyl complexes; anthraquinone-based dyes; and polycyclic quinine-based dyes.

9. The photoelectric device according to claim 8, wherein the xanthine-based dyes include rhodamine B, Rose bengal, eosin, or erythrosine; the cyanine-based dyes include quinocyanine or cryptocyanine; the basic dyes include phenosafranine, capri blue, thiosine, or methylene blue; and the porphyrin-based compounds include chlorophyll, zinc porphyrin, or magnesium porphyrin.

10. The photoelectric device according to claim 5, wherein A and A' are independently selected from the group consisting of halogen-substituted or unsubstituted tetraalkylammonium, benzyltrialkylammonium, and phenyltrialkylammonium, wherein the number of carbon atoms of an alkyl group bonded to the N atom is 1 to 20; and the alkyl groups bonded to the same N atom have the same or different lengths.

11. The photoelectric device according to claim 5, wherein the sum of m and n is greater than or equal to 3 and less than or equal to 4.

12. The photoelectric device according to claim 5, wherein A is tetrabutylammonium; A' is selected from the group consisting of tetramethylammonium, n- hexadecyltrimethylammonium and benzyltrimethylammonium; m is 2; and n is 1.

* * * * *